(12) United States Patent
Yang et al.

(10) Patent No.: US 9,060,498 B2
(45) Date of Patent: Jun. 23, 2015

(54) PTERYGIUM ANIMAL MODEL USING HUMAN PTERYGIAL EPITHELIAL CELLS

(71) Applicant: INJE UNIVERSITY INDUSTRY-ACADEMIC COOPERATION FOUNDATION, Gimhae-si, Gyeongsangnam-do (KR)

(72) Inventors: Jae Wook Yang, Busan (KR); Hye Sook Lee, Busan (KR); Ji Hyun Lee, Busan (KR)

(73) Assignee: INJE UNIVERSITY INDUSTRY-ACADEMIC COOPERATION FOUNDATION, Gyeongsangnam-Do (KR)

( * ) Notice: Subject to any disclaimer, the term of this patent is extended or adjusted under 35 U.S.C. 154(b) by 0 days.

(21) Appl. No.: 14/161,663

(22) Filed: Jan. 22, 2014

(65) Prior Publication Data

US 2015/0132225 A1      May 14, 2015

(51) Int. Cl.
*A01K 67/00* (2006.01)
*A01K 67/027* (2006.01)

(52) U.S. Cl.
CPC .................................. *A01K 67/0271* (2013.01)

(58) Field of Classification Search
CPC ........... A01K 67/0271; A01K 2267/03; A01K 2267/0331; C12N 5/0621; C12N 5/0625
USPC ........................................ 800/8, 13; 435/325
See application file for complete search history.

(56) References Cited

FOREIGN PATENT DOCUMENTS

KR      10-2013-0085598            7/2013

OTHER PUBLICATIONS

Di Girolamo et al. Br. J Ophthalmol 1999;83:1077-82.*
Pardo et al. Invest Ophathal Vis Sci 2008;49:3074-79.*

* cited by examiner

*Primary Examiner* — Janice Li
(74) *Attorney, Agent, or Firm* — Revolution IP, PLLC

(57) ABSTRACT

Provided is a pterygium animal model produced by injecting human-derived pterygial epithelial cells that are isolated and cultured in vitro. The animal model has characteristics similar to those of pterygium, which are observed only in humans, wherein such characteristics are caused in such a way that pterygial epithelial cells are isolated from human pterygium corneal tissues and cultured, the cultured pterygial epithelial cells are sub-cultured, and human-derived pterygial epithelial cells of which identify is confirmed are injected into the nasal subconjunctival space of mice. The pterygium animal model allows a pterygium therapeutic agent to be effectively screened.

6 Claims, 5 Drawing Sheets

PTERYGIUM ANIMAL MODEL USING HUMAN PTERYGIAL EPITHELIAL CELLS

RELATED APPLICATIONS

This application claims the benefit of Korean Patent Application No. 10-2013-0138084, filed on Nov. 14, 2013, in the Korean Intellectual Property Office, the disclosure of which is incorporated herein in its entirety by reference.

BACKGROUND

1. Field

One or more embodiments of the present invention are directed to an animal model induced to have pterygium, which is an ocular surface lesion observed only in humans, for use in researching pterygium and developing a therapeutic agent therefor.

2. Description of the Related Art

Pterygium is a wing-shaped ocular surface lesion characterized by the encroachment of conjunctival tissue over the cornea. This lesion is thought to originate from limbal stem cells that have been altered by chronic ultraviolet-B exposure, and is observed only in humans.

According to many studies, pterygium chemotherapeutic agents have the potential long-term risk of sight-threatening complications, and the current treatment for pterygium focuses excision, and prevention of recurrence which is achieved through surgical techniques to cover the bare scleral bed via grafts of autologous conjunctival, limbal tissue, or amniotic membrane.

Typical search on the occurrence and treatment for pterygium has been limited to either studies utilizing resected surgical tissue or in vitro culture cell model. As an animal model for the pterygium research, UVB-exposed animals, suture-stimulated animals, or chemical-burn animals were used. However, reliable lab animal models have not been established.

Therefore, to resolve these problems, inventors of the present application isolated human pterygial epithelial cells (hPEC) by surgical operations, cultured the cells, and after the confirmation of pterygial epithelial cells, injected the hPEC into mice.

SUMMARY

One or more embodiments provide an animal model that is useful and reliable for studies on the progress of pterygium, which is observed only in humans, and the development of a therapeutic agent for pterygium, wherein characteristics similar to those of human pterygium are provided to the animal model by injecting human-derived pterygial epithelial cells to the animal model.

Additional aspects will be set forth in part in the description which follows and, in part, will be apparent from the description, or may be learned by practice of the presented embodiments.

An aspect of the present invention provides a pterygium animal model obtained by injecting human-derived pterygial epithelial cells to the nasal subconjunctival space of mice.

Another aspect of the present invention provides a method of preparing a pterygium animal model, wherein the method includes: obtaining human pterygium tissue sections by a surgical operation; culturing the obtained human pterygium tissue sections in culture medium in vitro; isolating pterygial epithelial cells from the cultured tissue sections and sub-culturing the isolated pterygial epithelial cells; confirming identity of the passaged cultured pterygium epithelial cells; and injecting the confirmed human-derived pterygial epithelial cells into the nasal subconjunctival space of mice.

The passaged cultured human-derived pterygium epithelial cells may be identified by confirming that one or two or more genes selected from the group consisting of pan-CK (cytokeratin), CK3/2p, and vimentin are positively expressed.

The passaged cultured human-derived pterygium epithelial cells may include identified by confirming that CK13 is negatively expressed.

Another aspect of the present invention provides a method of screening a pterygium therapeutic agent by using the animal model.

A screened candidate material is injected into one eye of the animal model and a control material is injected into the other eye to confirm pterygium therapeutic effects of the candidate material.

BRIEF DESCRIPTION OF THE DRAWINGS

These and/or other aspects will become apparent and more readily appreciated from the following description of the embodiments, taken in conjunction with the accompanying drawings in which:

FIG. 3B is a graph of the lesion sizes (t-test at $**P<0.01$);

DETAILED DESCRIPTION

Hereinafter, one or more embodiments of the present invention will be explained in detail for better understanding. However, the following embodiments are provided herein for illustrative purpose only, and do not limit the scope of the present invention. Embodiments of the present invention are provided to one of ordinary skill in the art for the complete understanding of the present invention.

Reference Examples are presented herein to provide a reference example to a corresponding example of the present invention.

REFERENCE EXAMPLE

Statistical Analysis

Respective analyses were performed at least 3 times. Results obtained therefrom were analyzed by using SPSS version 18.0 manufactured by Windows (SPSS, Chicago, Ill.) and expressed as the ±standard deviation. The statistical significance was determined as p<0.05.

Example 1

Primary Culturing of Human Pterygial Epithelial Cells (hPECs)

hPECs were isolated from specimens during surgical removal and the cells were cultured. This study was performed after the approval of the institutional review board (IRB) of Busan Paik Hospital, Inje University College of Medicine, Busan, Korea, according to a protocol (IRB No.; 12128) also approved by IRB. All participants provided written informed consent after having received a comprehensive explanation of study procedures.

Fresh pterygium specimens were place in six-well culture plates containing 500 μL Dulbecco'S phosphate buffered saline (DPBS; Gibco, Carlsbad, Calif.), and then, the epithelium was separated from the underlying stroma and subsequently cut into several 1 to 2 mm$^2$ pieces. The cut epithelial tissue was cultured on surfaces of a culture plate coated with collagen (rat tail collagen type I; Sigma, St. Louis, Mo.) for three days in Dulbecco's modified Eagle's medium/F12 (DMEM/F12; Gibco) medium supplemented with 10% bovine calf serum (BCS; Gibco), 0.5% dimethyl sulfoxide (DMSO; Sigma), and 1% antibiotic/antimycotic (Gibco), and during the culturing time, the cells migrated from the explant to the culture plate.

Then, the explant was removed, and the medium was exchanged with keratinocyte-serum free medium with 5% BCS and 1% antibiotic/antimycotic to further promote epithelial cell growth.

When the cells were 60-80% confluent, they were passaged several times with 0.25% trypsin-EDTA (Gibco). The cells were then placed in DMEM/F12 medium supplemented with 5% fetal bovine serum (FBS; Hyclone, Logan, Utah), 0.5% DMSO, and 1% antibiotic/antimycotic. The medium was renewed every two to three days. During the passages, the cells were incubated at a temperature of 37° C. in an atmosphere of 5% $CO_2$.

Cell outgrowth from the explants was observed within two to three days in the collagen type 1-coated culture dish. By day 7, the explants exhibited a morphology typical of epithelial cells.

Figure 1:
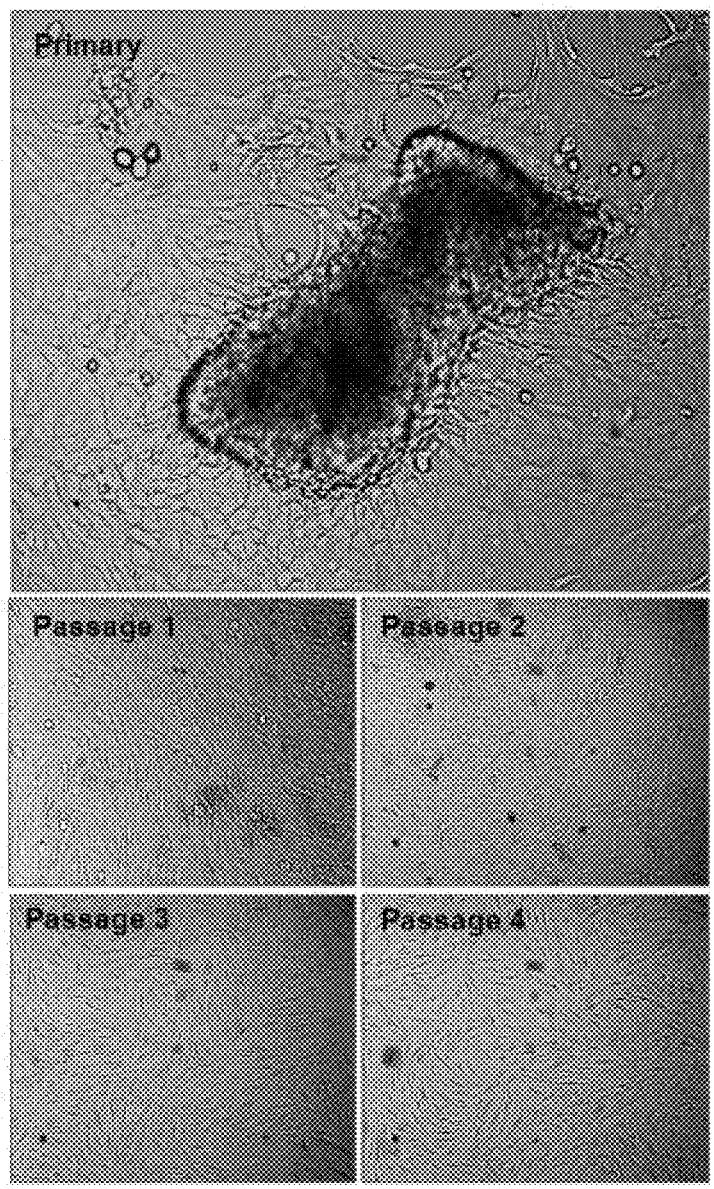
FIG. 1 shows micrographs exhibiting the morphology of primary and passaged human pterygial epithelial cells (hPECs), wherein all micrographs were obtained at a magnification of 100×.

After two weeks in primary culture, trypsin digestion was used for subculture. These subcultured hPECs grew rapidly and were subsequently passaged once weekly, and characteristics of cells were observed by using cells from passages 1 to 4, As a result, as shown in FIG. 1, the passaged hPECs were morphologically distinct from passage 3 compared to cells in the primary explants culture.

Example 2

Fluorescence Antibodies Analysis of Cultured Pterygial Epithelial Cells

Cultured hPECs were stained with pan-CK, CK3/2p, vimentin, and CK13 antibodies and then, immunofluorescence microscopy was performed thereon to confirm whether the cultured cells are pterygial epithelial cells.

For the identification of the hPECs, the cells were fixed with 3.5% paraformaldehyde, permeabilized with 0.1% Triton X-100, blocked with 2% bovine serum albumin (BSA; all from sigma), and incubated for 24 hours at 4° C. with the following primary antibodies; anti-pan-cytokeratin (pan-CK, 1:100; Santa Cruz, Calif.), anti-cytokeratin3/2p (CK3/2p; 1:100; Santa Cruz), anti-vimentin (1:200; Santa Cruz), and anti-cytokeratin 13 (CK13, 1:100; Santa Cruz).

After the incubation, the cells were washed with phosphate buffered saline (PBS; Gibco) and then, incubated for 1 hour with FITC-conjugated mouse immunoglobulin G secondary antibody (1:200; Santa Cruz).

The stained cells were counterstained with 4', 6-diamidino-2-phenylindole (DAPI; Invitrogen, Carlsbad, Calif.) and then, pterygial epithelial cells were confirmed by using an automatic FISH imager (BX51, Olympus, Tokyo, Japan).

As a result, as shown in FIG. 2A, it was confirmed that in all cells from passages, the pan-CK staining of the corneal epithelium was weakly positive, and as shown in FIG. 2B, CK3/2p was also weakly expressed. In particular, in cells from passage 3, CK3/2p decreased.

However, as shown in FIG. 2C, cytoplasmic immunostaining with vimentin was intensely present in all hPECs, but as shown in FIG. 2D, CK13, a marker of the conjunctiva epithelium, was negative in all passaged cells.

From these results, it was confirmed that passage 2 hPECs were appropriate for injection to nude mice.

Example 3

Production of Cornea Pterygium Animal Model 6-week old male athymic nude mice were obtained from Taconic Farms, Inc. (Germantown, N.Y.), and this experiment was conducted in accordance with guidelines for animal experiments approved by Inje University College of Medicine and the ARVO statement for the use of animals in ophthalmic and vision research.

To develop pterygial epithelial cells, 1×10$^4$ passage 2 hPECs which were cultured according to Example 1 and confirmed according to Example 2 were injected into the nasal subconjunctival space in athymic nude mice. The mice were euthanized by injection of zoletil 50 (10 mg/kg; Virbac Laboratories, Carros, France), and an eye drop of alcaine (Alcon Inc., Seoul, Korea) for subconjunctival injection.

Example 4

Preparation of Chondrocyte-Derived Extracellular Matrix (CDECM)

ECM scaffold was prepared from portcine chondrocytes according to a known method (Jin C Z, Park S R, Choi B H, Park K D, Min B H (2007) In vivo cartilage tissue engineering using a cell-derived extracellular matrix (ECM) scaffold. Artif Organs 31:183-92). In detail, first, primary chondrocytes from porcine knee joints were first expanded in a monolayer culture for three weeks and further cultured in a three dimensional (3-D) pellet for another three weeks. The 3-D cartilage-like tissue was freeze-dried for 48 hours at −56° C. under 5 mTorr to remove cellular components of, for example, a 3-D cartilage, thereby producing a porous, sponge type scaffold.

Example 5

Confirmation of CDECM Effects by Comparing Lesion Sizes of Pterygium Animal Model Cornea CDECM dissolved in PBS (25 mg/mL, 10 μL) was injected to the nasal subconjunctival space in the right eye 7, 10 and 14 days after the injection of pterygial epithelial cells (hPECs), and as a control, PBS (10 μL) was injected to the same area of the opposite eye on the same schedule as the left eye.

Image analysis of the photograph was performed using ImageJ® to compare the lesion size, and the results were calculated as the ratio of pterygium to the entire cornea.

Figure 3:
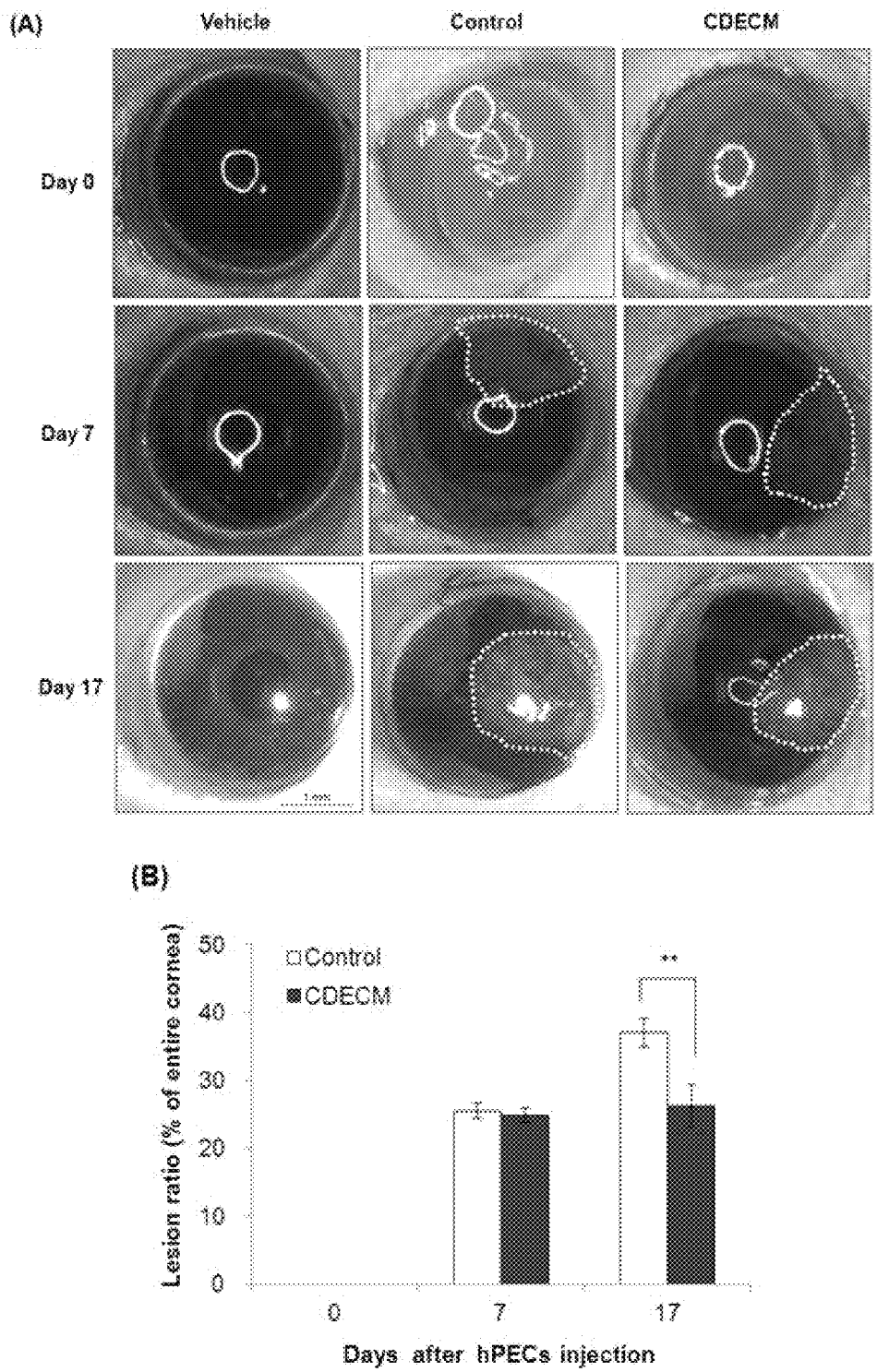
FIGS. 3A and 3B show chondrocyte-derived extracellular matrix (CDECM) effects on the pterygium mouse model, wherein FIG. 3A show images of the animal model 7, 10, 14 and 17 days after human pterygial epithelial cell injection, in a CDECM group and a control group, to compare pterygium lesion sizes thereof.

Pterygial lesion in mouse model was confirmed seven days after subconjunctival injection of the hPECs. However, there was no significant difference in the lesion size: as shown in FIG. 3, the ratio of the lesion area to the entire cornea in the ECM group was 25.5% and that in the control group was 24.9%.

On day 10 after hPECs injection, the lesion size was also not significantly different between both groups. However, the lesion area relative to the entire cornea was significantly different between the control group (34.3%) and the ECM group (26.7%) at day 10 after hPECs injection.

On day 17 after epithelial cell injection, the lesion size compared to the entire cornea was increased to 37.1% in the control group, while in the ECM group, the lesion size corresponded to 26.3% of the area of the cornea (an increase of 11.6% and 1.4% from the baseline, respectively, $P<0.01$).

For histologic examination, the eyes were fixed in 3.5% paraformaldehyde, and embedded in an optimal cutting temperature compound (OCT; Tissue-Tek, Sakura Fine Technical Co., Ltd., Tokyo, Japan) 17 days after hPEC injection, and then, the tissues were frozen with liquid nitrogen.

Example 6

Confirmation of CDECM Effects by Analyzing Histological Change and Immunohistochemistry Results of Pterygium Animal Model Cornea Serial sections (8 μm) were deparaffinized with xylene and stained with hematoxylin and eosin, and tissue sections cut at 6 μm were used for immunohistochemistry analysis.

First, the sections were fixed with pre-cooled acetone for 5 minutes, and incubated for 1 hour with the primary antibody solution shown in Table 1. Then, the sections were incubated with the secondary antibody (DAKO Corp, Glostrup, Denmark) for 45 minutes.

The immunoreactions were visualized with diaminobenzidine (DAB) chromogen, and the sections were counterstained with Mayer's hematoxylin (Sigma) for 30 seconds at room temperature. Images of the sections were photographed with a Virtual Microscope (NanoZoomer 2.0 RS, Hamamatsu, Japan).

Figure 4:
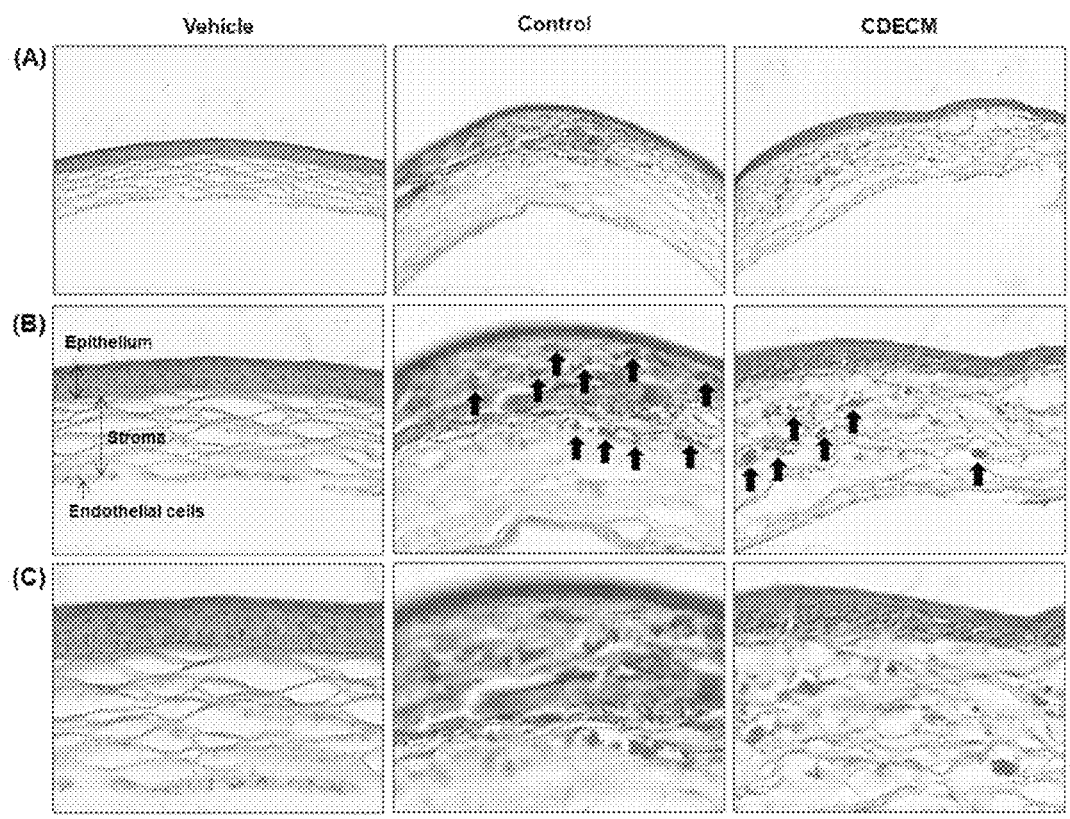
FIG. 4 shows CDECM effects confirmed by pathological change caused by treating the pterygium mouse model cornea with CDECM, wherein arrows indicate new blood vessels.

From the histological examination results, it was confirmed that as shown in FIG. 4, the pterygium mice control showed a thin overlying epithelium compared with a normal group, epithelial cells extending into the superficial stroma, neo-vessels, and extracellular matrix breakdown. However, in the CDECM group, but these alterations of the histology after hPECs injection were suppressed by CDECM.

Figure 5:
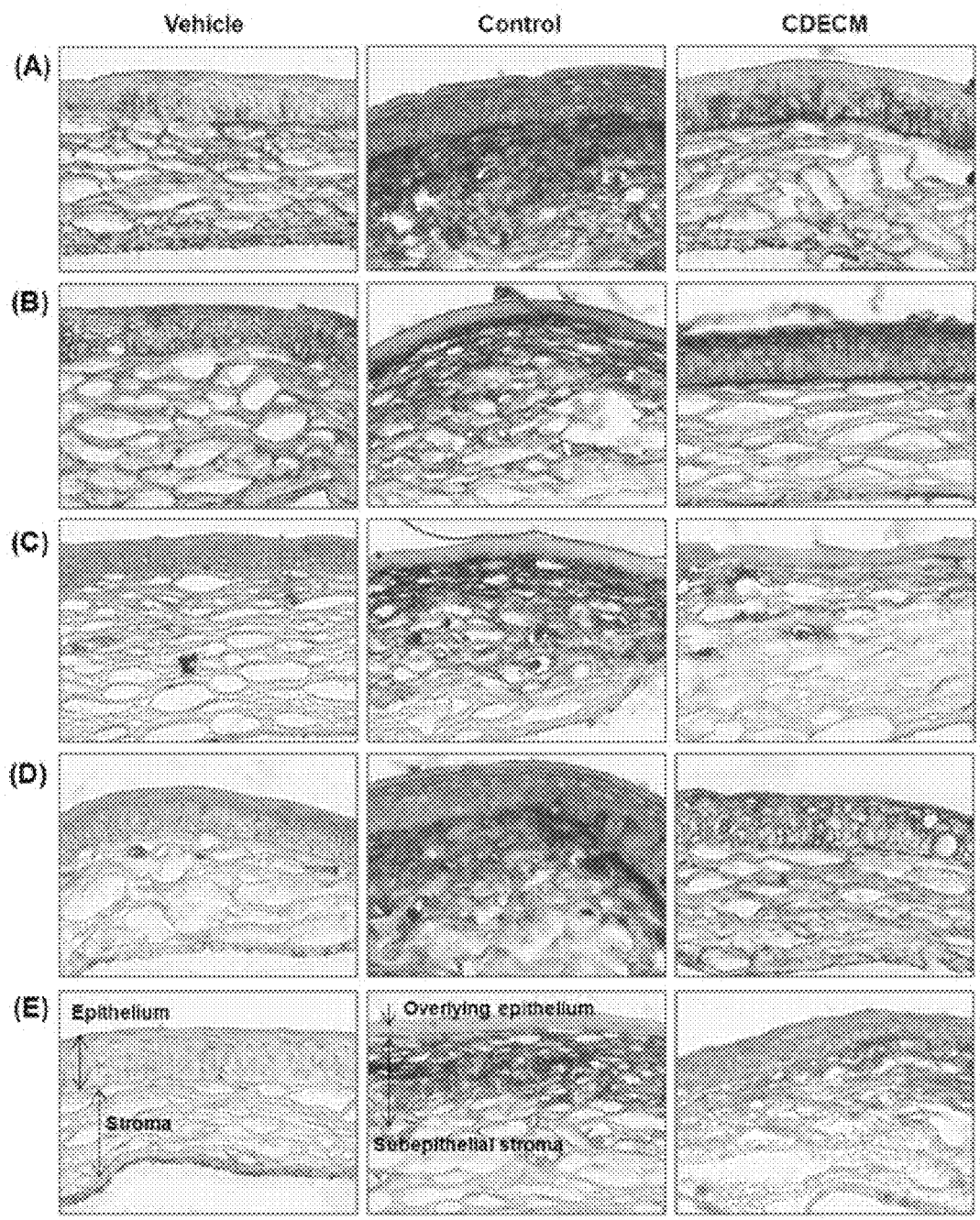
FIG. 5 shows results obtained by immunochemistry-staining with CD31(A), pan-CK(B), CK3/2p(C), vimentin (D), and mucin-1(E) pterygium mouse model treated with CDECM, wherein micrographs of the animal model were obtained at a magnification of 630×.

Also, when as shown in FIG. 5, the corena area was immunostained with antibodies against cluster of differentiation 31 (CD31), pan-CK, CK3/2p, and vimentin.

The neovascularization marker, CD31, was overexpressed in the overlying epithelium and subepithelial stromal cells of the pterygium mice control group. However, in the CDECM group, as shown in FIG. 5A, the expression level of CD31 declined in the subepithelial stromal cells. Also, referring to FIGS. 5B and 5C showing immunostaining results of pan-CK and CK3/2p, in the subepithelial stromal cells of the cornea of the pterygium control group, immunostaining of pan-CK and CK3/2p was intensely present, but in the CDECM group, they were significantly decreased.

Also, even in FIGS. 5D and 5E showing staining results of vimentin and mucin-1, it was confirmed that compared to the control, in the CDECM group, vimentin and mucin-1 were intensely suppressed in the subepithelial stromal cells of the cornea.

TABLE 1

Antibodies used in the immunohistochemistry of the cornea from pterygium mice

| Antibody | Dilution | Type of antibodies | Immunized animal | Company |
| --- | --- | --- | --- | --- |
| CD31 | 1:200 | Polyclonal | Rabbit | Bioss |
| pan-CK | 1:200 | Monoclonal | Mouse | Santa Cruz |
| CK3/2p | 1:200 | Monoclonal | Mouse | Santa Cruz |
| Vimentin | 1:200 | Monoclonal | Mouse | Santa Cruz |

According to one or more embodiments of the present invention, human-derived pterygial epithelial cells obtained by culturing human pterygium corneal tissue sections are injected into the nasal subconjunctival space of an animal to easily induce pterygium, which occurs only in humans, in animals, thereby providing an animal model showing characteristics similar to those of human pterygium. By doing so, the animal model can be useful for research on pterygium and screening of pterygium therapeutic agent.

Figure 2:
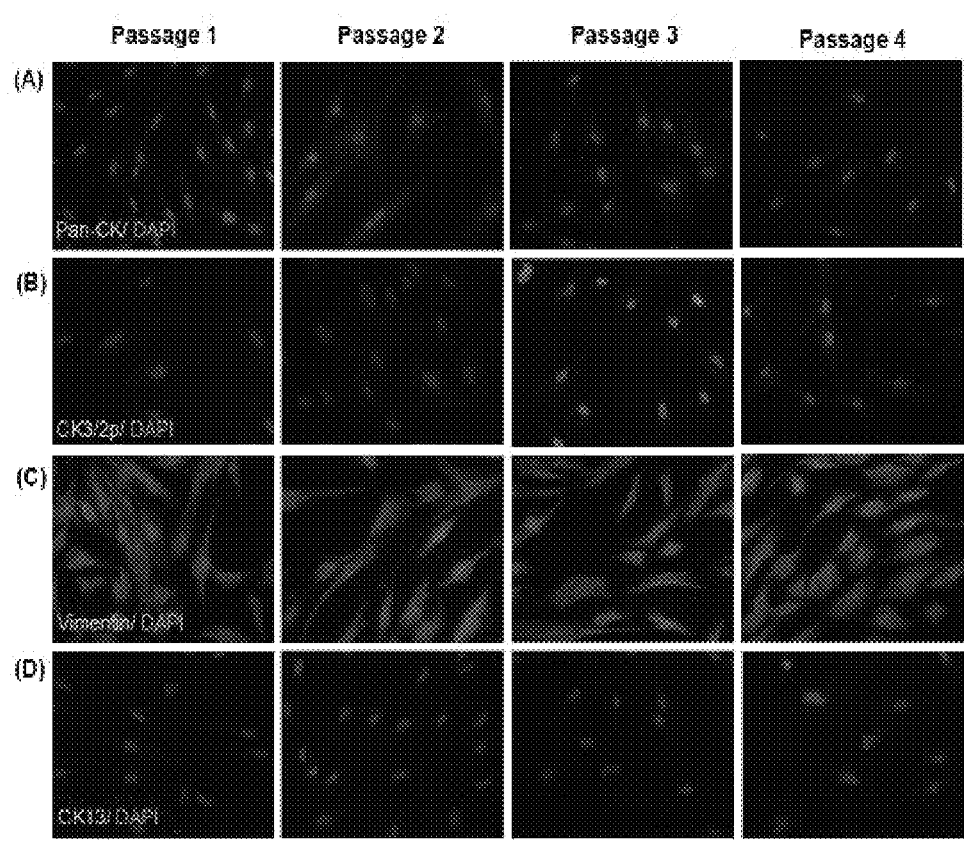
FIG. 2 shows micrographs of cultured hPECs which were immunostained with pan-CK (A), CK3/2p (B), vimentin (C) and CK13 (D), according to passage, wherein all micrographs were obtained at a magnification of 400×.

In detail, referring to FIG. 5 showing immunochemical staining results of the cornea of a pterygium mouse model into which human-derived pterygial epithelial cells are injected, as shown in FIG. 2, as in immunofluorescence staining results of cultured hPECs, the cells in the mouse model were positive for pan-CK, CK3/2p, and vimentin and negative for CK13.

Also, as shown in FIGS. 3 to 5, when one eye of an animal model according to the present invention is treated with CDECM, which is a candidate for a pterygium therapeutic agent, and the other eye is treated with PBS as a control, it was confirmed that the use of the animal model has lead to significant effects in screening of a pterygium therapeutic agent.

From these results, it was confirmed that a mouse model having pterygium induced by using hPECs has characteristics similar to those of human pterygium and accordingly, the mouse model is suitable for use in research into pterygium and development of a pterygium therapeutic agent by therapeutic agent screening.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A pterygium animal model obtained by injecting pterygial epithelial cells into a nasal subconjunctival space of athymic nude mice.

2. A method of preparing a pterygium animal model, the method comprising:

obtaining human pterygium tissue sections by a surgical operation;

culturing the obtained human pterygium tissue sections in culture medium in vitro;

isolating pterygial epithelial cells from the cultured tissue sections and sub-culturing the isolated pterygial epithelial cells;

confirming identity of passaged cultured pterygium epithelial cells; and injecting the confirmed pterygial epithelial cells into a nasal subconjunctival space of athymic nude mice.

3. The method of claim 2, wherein the passaged cultured pterygium epithelial cells are identified by confirming that the passaged cultured pterygium epithelial cells are positive for one or two or more genes selected from the group consisting of pan-CK (cytokeratin), CK3/2p, and vimentin.

4. The method of claim 2, wherein the passaged cultured pterygium epithelial cells are identified by confirming that the passaged cultured pterygium epithelial cells are negative for CK13.

5. A method of screening a pterygium therapeutic agent by using the animal model of claim 1, comprising administering the pterygium therapeutic agent to the animal model,
wherein the administered agent as a candidate material is injected into one eye of the animal model.

6. The method of claim 5, further comprising injecting a control material into the other eye of the animal model to confirm pterygium therapeutic effects of the candidate material.

* * * * *